US010206387B2

(12) United States Patent
Kommisrud

(10) Patent No.: US 10,206,387 B2
(45) Date of Patent: Feb. 19, 2019

(54) METHOD FOR CRYOPRESERVATION OF BIOLOGICAL MATERIAL

(71) Applicant: Cryogenetics AS, Hamar (NO)

(72) Inventor: Elisabeth Kommisrud, Stange (NO)

(73) Assignee: Cryogenetics AS, Hamar (NO)

( * ) Notice: Subject to any disclaimer, the term of this patent is extended or adjusted under 35 U.S.C. 154(b) by 604 days.

(21) Appl. No.: 14/748,243

(22) Filed: Jun. 24, 2015

(65) Prior Publication Data

US 2016/0021875 A1    Jan. 28, 2016

Related U.S. Application Data

(62) Division of application No. 12/996,773, filed as application No. PCT/NO2009/000216 on Jun. 10, 2009, now abandoned.

(30) Foreign Application Priority Data

Jun. 10, 2008  (GB) .................................. 0810606.4

(51) Int. Cl.
  *A01N 1/02*  (2006.01)
  *A61D 19/02*  (2006.01)
  *B65D 75/52*  (2006.01)

(52) U.S. Cl.
  CPC ......... *A01N 1/0268* (2013.01); *A61D 19/022* (2013.01); *B65D 75/527* (2013.01)

(58) Field of Classification Search
  CPC .. A01N 1/0268; A01N 1/0263; B65D 75/527; A61D 19/022
  USPC ............................. 435/2; 220/560.08; 53/440
  See application file for complete search history.

(56) References Cited

U.S. PATENT DOCUMENTS

| 5,364,385 A * | 11/1994 | Harms ...................... A61J 1/05 604/403 |
| 2008/0103428 A1* | 5/2008 | Delaronde-Wilton ...................... A61M 1/0209 604/6.03 |
| 2009/0148934 A1* | 6/2009 | Woods ..................... A01N 1/02 435/307.1 |
| 2010/0124564 A1* | 5/2010 | Martinson .............. A61K 35/39 424/424 |

* cited by examiner

*Primary Examiner* — Robert Long
*Assistant Examiner* — Xavier A Madison
(74) *Attorney, Agent, or Firm* — Christian D. Abel

(57) ABSTRACT

A method for cryopreservation of biological material where a sample of a biological material is inserted into a packaging having two substantially parallel walls spaced from 2.5 mm apart or less, the walls connected to each other along a substantially part of their periphery and including a plurality of internal ridges for directing the flow of material through the packaging. After the material is evenly distributed in the package, the material is frozen for cryopreservation of biological material.

7 Claims, 3 Drawing Sheets

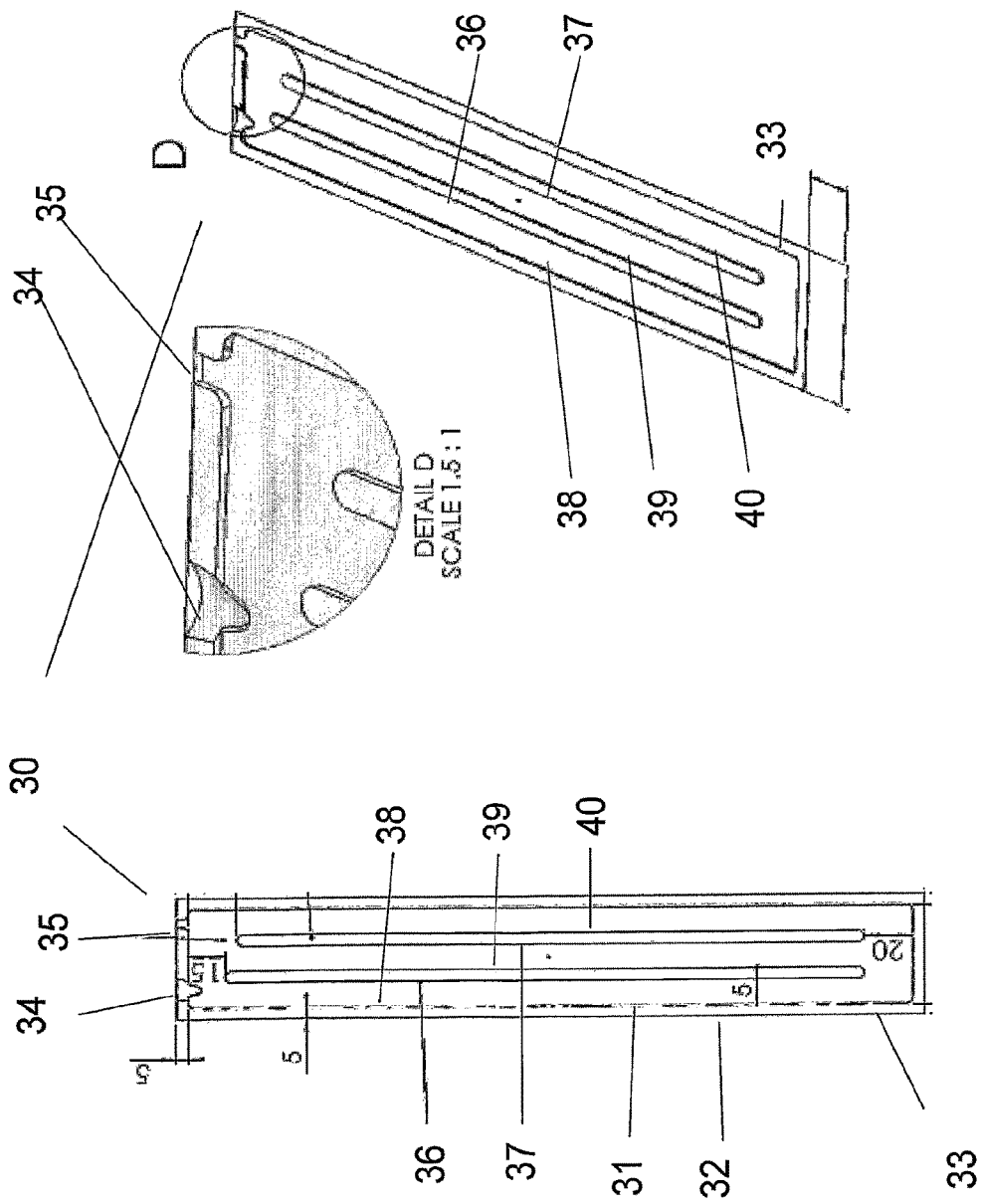

METHOD FOR CRYOPRESERVATION OF BIOLOGICAL MATERIAL

CROSS REFERENCE TO RELATED APPLICATIONS

This application is a Divisional application of U.S. application Ser. No. 12/996,773, filed 8 Dec. 2010, which is a US National Stage application of PCT/NO2009/000216, filed 10 Jun. 2009.

BACKGROUND

The present invention relates to a packaging for storing, transport and/or freezing of a biological material such as fish semen or milt. More particular, the invention regards a packaging for cryopreservation of spermatozoa, embryos or eggs from aquatic organisms.

Traditionally, semen or milt are cryopreserved in cryogenic straw consisting of a narrow and slender tube as for example disclosed in EP 0 873 726 A1, EP 0,562,947 A1, U.S. Pat. No. 5,868,178, and U.S. Pat. No. 5,190,880. The main drawback with these straws is the fact that only small volumes of biological material can be filled into these straws.

Usually, 0.50-1.2 ml semen are frozen in conventional medium cryogenic straw. Trials have been performed freezing 5 ml in comparison with 1.2 ml, resulting in a dramatic decrease in fertilization success (Lahnsteiner et al, 1997: Aquaculture Research 28, 471-479). The aquaculture industry need an efficient large scale cryopreservation protocol and thus preferably a method and means which enables cryopreservation of larger amounts of semen.

Furthermore, it is a well accepted fact that larger and less narrow straw would not be useful since they cannot provide sufficient uniform freezing of the content (e.g. semen), and thus causes reduced quality of the cryopreserved material.

For animal semen, pouches have been proposed for packaging and later artificial insemination of animals. One example of such a pouch is shown in U.S. Pat. No. 7,150,734 and DK/EP 0605406. However, these pouches are not suited for cryopreservation, as the volume is too large to ensure uniform freezing of the full content.

BRIEF SUMMARY OF THE INVENTION

The object of the invention is to provide a packaging for biological material which contains a significant volume while ensuring a uniform temperature of the whole content, for example during freezing and thawing. A significant volume in this context will depend on the type of biological material, for example varying between species, but is of at least 5 ml.

In the following description, the advantages of the invention is described when used in connection with freezing the biological material, for example for cryopreservation, but it will be obvious for the skilled person that the packaging according to the invention can be used for other purposes such as long and short time storage and transport.

The object of the invention is achieved by means of the features of the patent claims.

According to the invention, there is provided a packaging for biological material which comprises two substantially parallel walls connected to each other along a substantially part of their periphery and in at least a central area.

The biologic material is for example semen, embryos, eggs, etc. The invention is particularly suitable for cryopreservation of spermatozoa collected from aquatic species. Aquatic species are in this context any organism living in water and wherein reproduction is performed by the joining of spermatozoa and egg from a male and female animal, respectively, herein organisms employing oviparous, ovoviviparous or viviparous reproduction. The present invention allows packaging of male gametes (sperm) collected from marine, anadromous and fresh water fish. However, the invention is not limited to fish species, but also includes other water-dwelling organisms such as Crustacea, inter alia crabs, lobsters, crayfish, shrimps, shellfish and barnacles, and Mollusca, inter alia gastropods such as abalone, cephalopods such as octopus, and bivalves such as scallops, clams and oysters.

Non-limiting examples of oviparous fish species are inter alia Salmonidae, such as Atlantic salmon (*Salmo salar* L.) and rainbow trout (*Onchorhyncus mykiss*), Gadidae, such as Atlantic cod (*Gadus morhua*) and haddock (*Melanogrammus aeglefinus*) and Cichlidae, such as Nile tilapia (*Oreochromis niloticus niloticus*). Non-limiting examples of ovoviviparous fish include inter alia Poecilidae, such as guppy (*Poecilia reticulata*) and Squatinidae, such as angel sharks (*Squatina* spp.). Non-limiting examples of viviparous fishes includes coelacanths (*Latimeria chalumnae*), Goodeidae (splitfins), Embiotocidae (surf-perches) and Carcharhinidae (requiem sharks).

The parallel arrangement of the walls provides an evenly distribution of the biological material to be frozen. The distance separating the walls decides the thickness of the layer of biologic material, thus a small distance provides a thin layer of biological material and thus a uniform freezing of the content. The walls may have any shape and may be straight or not, i.e. wavy, as long as they are parallel and provide an evenly distribution of a thin layer of e.g. semen/milt.

In one embodiment, the walls are separated by a distance between the inner surface of the two walls which is about 2 mm, for example about 1.1 mm, about 1.0 mm, or about 0.95 mm.

The distance separating the walls depend on which cooling rate that is contemplated, the material of the device, to which degree the device is filled etc. The distance may also be about 1 or 2 mm. Furthermore, by using a flexible material which enables a certain expansion of the device upon freezing of the contained semen, the distance may vary from about 0.95-2 mm The biological material, such as sperm cells is thus evenly and sparsely distributed between the walls of the device. The device according to the present invention thus provides an equal temperature curve for all the sperm cells contained in the present device throughout a full freezing and thawing period. Such evenly and sparsely distribution and corresponding equal temperature curves may be obtained also by use of conventional cryogenic straw consisting of a narrow and slender tube. However, equal temperature curves for all cells during the entire freezing and thawing procedure will not be possible to obtain with conventional straw when the volume of each straw is increased beyond 0.5 ml.

The packaging may have one or more openings. The openings may be arranged for filling the packaging by means of a filling device, applying suction, draining air, etc.

An opening for filling the packaging may be provided any suitable place in the packaging. In one embodiment the opening is placed in the periphery of the packaging, for example in one side. The opening may be in a closed state prior to filling the packaging, thus preventing contamination of the inner surfaces/the inside of the packaging and ensuring sterile conditions if desired. This may be embodied by welding the outer part of the opening during production of the packaging. The end that is being used for the filling of the device is then cut shortly before the filling of the device.

In one embodiment, the opening may extend over a substantial part of one surface of the packaging, for example by one of the walls being temporarily detached/not yet connected to the packaging. In this case, the opening is closed after filling the packaging by connecting the second wall to the first wall, for example by means of welding.

In one embodiment, the walls are quadrilateral and connected with each other along at least three sides and that the opening for filling the packaging is arranged in the fourth edge.

In one embodiment, an opening for draining air is arranged in the same side edge of the periphery of the packaging as the opening for filling the packaging.

As the shape of the walls decides the shape of the packaging, the walls are in one embodiment shaped in such a way that effective handling, e.g. such as for cryopreservation procedures or long time storage in liquid nitrogen, for example for transport is facilitated.

In one embodiment the length of the walls are at least about 15 times longer than the width, preferably about 12 times longer than the width.

The walls may for example be shaped as sheets. The walls should be semi-rigid, i.e. have certain stiffness in order to be able to maintain the parallelism between the walls, while also having a certain flexibility in order to be able to allow the biologic material to expand.

The walls may be connected to each other by means of welding, for example pulse welding, gluing, folding, or a combination of theses methods.

The walls are connected to each other in at least a central connection area, for example by welding. The connected area may be a narrow section, for example along the centre line/axis of the walls, or along a number of lines. The connection area may also be constituted by a number of point connections or a number of larger connection areas. Having more than one connection area is particularly useful if the packaging is relatively large. If the walls have an elongated shape, the central connection area may be along the longitudinal centre axis/line. The central connection area is in most embodiments separate from the periphery, allowing the biological material to flow between the periphery and the central connection area. In the case of a number of connection areas, the connection areas may be separate, allowing the biological material to flow also between and/or round the connection areas.

The shape and size of the central connection area can vary according to the shape and size of the walls and thus the packaging. A larger packaging may need a higher number of connection areas and/or larger connection areas. The connection of the walls in this central area ensures that the walls stay parallel after filling of the packaging and through subsequent processing of the packaging, thus ensuring the evenly and sparsely distribution of the biological material. With parallel is in this description meant that the thickness over the packaging varies little and/or do not exceed a required/desired thickness. For example may the maximum thickness be 1 mm or 2 mm. The distance between the connection areas must be adapted to the allowable thickness expansion of the packaging when filled. In one embodiment the distance between the connection areas are less than 3 mm, or less than 2 mm.

The shape and arrangement of the central connection area may also be adapted for guiding the flow of biological material during filling of the packaging. For example may one or several longitudinal shaped central connection areas form channels inside the packaging. Such channels may lead the flow of biological material in a desired path, for example to ensure complete filling of the packaging and drainage of air through an air draining opening.

In one embodiment the packaging comprises a funnel, for example arranged in one side. The funnel may be arranged in the opening or replacing the opening, thus being the opening.

In one embodiment of the invention, the opening is arranged to be closed subsequent to the filling, for example by pulse welding. There may also or alternatively be provided a closing device in the end, such as a plug.

In one embodiment, the external thickness of the packaging in empty state is no larger than about 2.5 mm, preferably 1.3 mm.

The material used for the manufacturing of the packaging should be leak proof and impermeable.

The packaging is in one embodiment made of a biocompatible, non-toxic material of food grade.

Examples of materials for making the packaging are: polyethylen terephtalate glycol (PETG), polyethylene, thermoplastic polyesther, (PET) polyvinyl chloride (PVC) or high securing ionomeric resine (IR), PEG, PE, or any combinations thereof.

In one embodiment, at least one of the walls is made of PET, and the inner surface of said walls are coated with PE.

In still another embodiment, one of the sheets/walls is made of PET and the other opposite sheet/wall is made of PE or vice versa. The use of both PET and PE in the production of the device facilitates the closing of the device by pulse welding subsequent to filling of biological material.

For identification purposes, the cryogenic device may furthermore be provided with suitable identification means such as combinations of codes and colours, barcodes and/or alphanumeric codes. The identification marks or systems must furthermore be resistant to long term storing in e.g. liquid nitrogen.

In one embodiment, a number of packagings are connected to each other along their sides and side by side, thus forming a packaging sheet. The characteristics of each of the packagings are as described above.

The number of packagings in one packaging sheet can vary depending on the needed volume or which type of biologic material that should be packaged.

The connection of the packagings may be performed during production, for example by providing two parallel films which will constitute the walls of the packagings and forming the individual packagings by providing welds or other connections between the two films in the areas constituting the sides and the central connection area. There may also be provided perforations between the individual packagings in order to facilitate separation of the packagings.

After being manufactured, the packagings of the invention may be sterilized, for example by using gamma rays or by ionization or other suitable methods well known to the person skilled in the art. Then the packagings are packed in a manner to avoid contamination.

In one embodiment the packaging for cryopreservation of biological material is filled by means of the following steps:
    filling the biological material between two substantially parallel walls connected to each other along a substantially length of their circumference through an opening,
    closing the opening.

The filling of biologic material between the walls may be done by conventional methods well known to the person skilled in the art. The filling may be performed manually, for example by an operator using a syringe or cannula, or automatic. Furthermore, the filling of a packaging sheet may preferably be done in one operation. The filling of all individual packagings may be performed simultaneously by using an automatic filling apparatus. In one embodiment, the apparatus direct several cannulas into the packagings and a predetermined volume of semen, e.g. 5 ml or 7 ml, is injected into each. Then the cannulas are drawn out and the openings are closed by e.g. pulse welding. The sheet may then be cut into separate packagings prior to further handling, storing etc.

In one embodiment, the biological material is filled between the parallel walls with a controlled flow rate.

The packagings according to the various embodiments of the invention may also be filled by applying suction to one end and then close the end thereafter in the same way as the filling of conventional cryogenic straw. There may also be arranged suction in one opening of the packaging while another opening is used for filling.

Subsequent to the filling of the biologic material, the packaging is closed, e.g. by autogenic heat sealing at one or both ends using sealing equipment well known to the person skilled in the art, such as by melting the end together by welding, for example ultrasound welding, high frequency welding, contact welding, etc. Also, the packaging may be provided with a closing device in the end, such as a plug used to close the ends of common cryogenic straw. The end must then be adjusted to fit a suitable plug. Such adjustments are well within the knowledge of the person skilled in the art.

BRIEF DESCRIPTION OF THE DRAWINGS

The invention will now be described in more detail by means of an example and by reference to the accompanying figures.

FIG. 3 shows another embodiment of a packaging according to the invention.

DETAILED DESCRIPTION OF THE INVENTION

Figure 1:
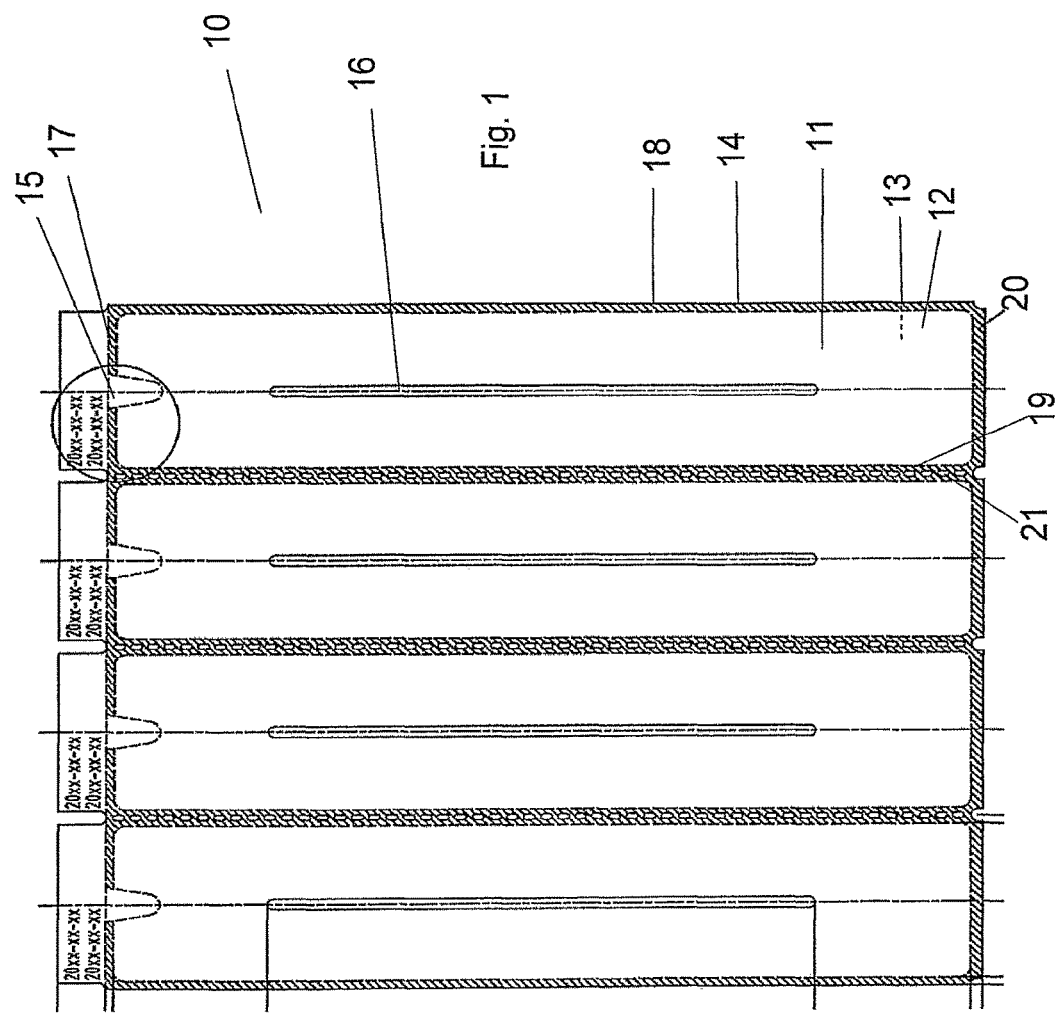
FIG. 1 shows one embodiment of the invention comprising a packaging sheet

FIG. 1 shows one embodiment of the invention comprising a packaging sheet 10 comprising four packagings 11 for cryopreservation of biological material. Each of the packagings 11 comprise two substantially parallel walls 12, 13 connected to each other along a substantially part of their periphery 14 and have an opening 15 for filling the packaging. The walls are further connected to each other in a central area 16.

In this particular embodiment, the walls 12, 13, and thus the packagings 11, are quadrilateral and elongated and the opening 15 is arranged in one of the end sides 17. The walls 12, 13 are connected along the three remaining sides 18, 19, 20.

The central connection area 16 is in this embodiment an elongated area reaching over a substantial length along the longitudinal central axis of the packaging.

The packagings 11 are connected to each other along their longitudinal sides 18, 19 and thus arranged side by side. In this embodiment, there are provided a perforation 21 between the individual packagings 11 enabling separation of the packagings before or after filling.

Figure 2A:
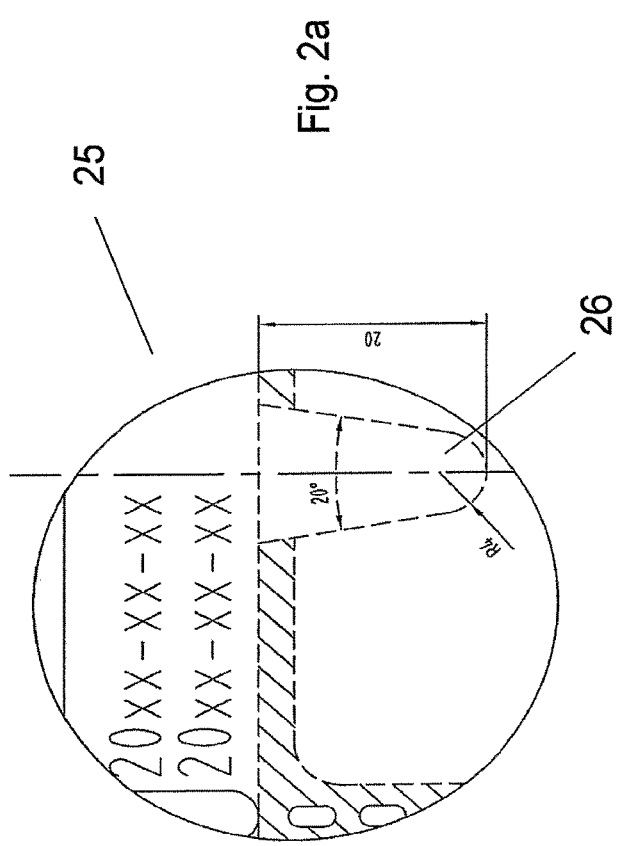
FIGS. 2a and 2b show an example of an opening for filling a package according to the invention.
Figure 2B:
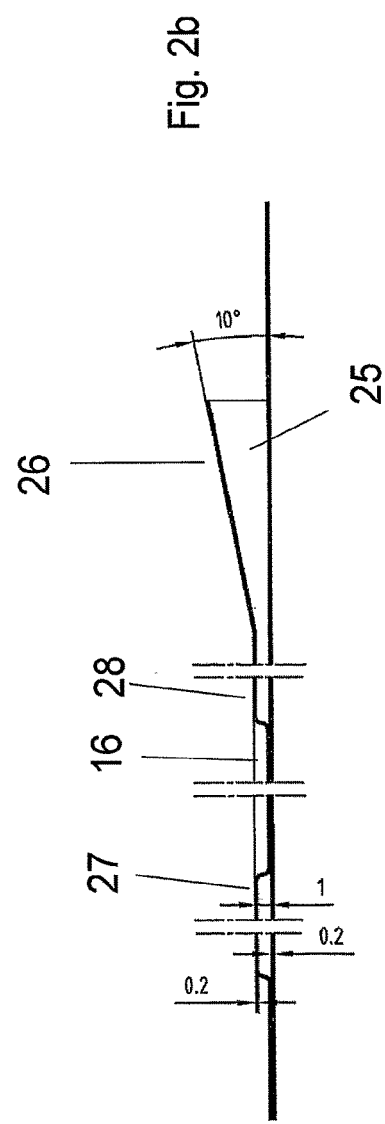

FIG. 2a shows details of an embodiment of an opening 25 in a packaging according to the invention. The opening 25 is in this embodiment shaped as a funnel 26 in order to facilitate the filling of the packaging. FIG. 2b is a longitudinal cross section of the device and illustrates the profile of the packaging along the opening 25, the parallel walls having a distance between them at 27 and 28, and the central connection area 16 where the walls are connected, thus having no distance between them.

FIG. 3 shows one embodiment of a packaging 30 according to the invention. In this embodiment, the packaging 30 comprises two substantially parallel walls 31, 32, connected to each other along a substantially part of their periphery 33. The packaging 30 has an opening 34 for filling the packaging and an opening 35 for draining air, the openings extending through the periphery of the packaging. The packing 30 has a rectangular form and the opening 34 for filling the packaging and the opening 35 for draining air are located in one end of the packaging. The walls 31, 32 are connected in a central area constituted by two longitudinal connection areas 36, 37. The longitudinal connection areas 36, 37 are in this embodiment arranged in parallel with each other and with the long sides of the periphery 33 of the packaging, thus forming three separate "channels" 38, 39, 40 in the packaging 30. The longitudinal connection areas are located offset from the location of the openings 34, 35 for filling the packaging and for draining air, respectively. The longitudinal connection areas 36, 37 are narrow, such that the area of the walls which are not connected are larger than the total connection area. As an example, the breadth of the longitudinal connection areas 36, 37 may be of the same magnitude as the breadth of the connected periphery, for example 5 mm. The breadth of the total packaging may for example be 40-50 mm and the length may be 300-320 mm.

The longitudinal connection areas 36, 37 have in this embodiment slightly different length, the longest connection area 37 being arranged closest to the opening 34 for filling the packaging and reaching nearer towards the packaging end with the two openings. With the connection area 37 being located offset to the right from the opening 34 for filling the packaging, the biological material will flow into the first channel 38 and subsequently into the second 39 and third 40 channel from the other end of the packaging. In this way, any air in the packaging will be pushed towards the opening 35 for draining air, thus ensuring that little or no air is left in the packaging after filling.

In other embodiments, the longest connection area may reach to and be connected to the connected periphery of the packaging or the two connection areas may have the same length.

Other embodiments are also possible, for example where the openings are arranged in the long edge of the packaging and the central connection areas are a number of longitudinal areas parallel to the short edges.

The invention claimed is:

1. A method for cryopreservation of biological material, wherein said biological material is semen, comprising
   a. providing a package for receiving a fluid sample of biological material, said package comprising
      i. two parallel, at least semi rigid sheets, spaced 2.5 mm apart or less, the sheets being substantially sealed around their periphery, said sheets having a first and a second end arranged at a distance therebetween,
      ii. a first opening arranged at the first or second end for the introduction of the sample, iii. one or more internal ridges arranged between the sheets, at least one of said ridges being shorter than the distance between said first and second ends of the sheets, said at least one ridge being arranged such that an unsealed space is formed between the ends of the at least one ridge and the ends of the sheets, the ridges being arranged to direct the flow of the sample throughout the package;

b. introducing the sample into the first opening, such that the sample flows throughout the package under influence of the ridges, wherein the two parallel sheets remain parallel after introduction of the biological material, c. sealing package, d. freezing the sample.

2. The method according to claim 1, wherein the package further comprises a second opening arranged for expulsion of air, and wherein the method further comprises expelling air from the second opening upon introduction of the sample and wherein the step of sealing the package comprises sealing the first and second openings.

3. The method according to claim 2 further comprising applying suction to the second opening in order to influence the flow of the sample throughout the package.

4. A method for cryopreservation of biological material, comprising a. Receiving a package filled with a fluid sample of biological material comprising semen, said filled package comprising i. two parallel, at least semi rigid sheets, spaced 2.5 mm apart or less, the sheets being substantially sealed around their periphery, said sheets having a first and a second end arranged at a distance therebetween, ii. one or more internal ridges arranged between the sheets at least one of said ridges being shorter than the distance between said first and second ends of the sheets, said at least one ridge being arranged such that an unsealed space is formed between the ends of the at least one ridge and the ends of the sheets, b. freezing the sample.

5. A method for cryopreservation of biological material comprising semen, comprising a. providing a package for receiving a fluid sample of biological material, said package comprising i. two parallel, at least semi rigid sheets, spaced 2.5 mm apart or less, the sheets being substantially sealed around their periphery, said sheets having a first and a second end arranged at a distance therebetween, ii. a first opening arranged for the introduction of the sample, iii. one or more internal ridges arranged between the sheets, at least one of said ridges being shorter than the distance between said first and second ends of the sheets, said at least one ridge being arranged such that an unsealed space is formed between the ends of the at least one ridge and the ends of the sheets, the ridges being arranged to direct the flow of the sample throughout the package;

b. introducing the sample into the first opening, such that the sample flows throughout the package under influence of the ridges, wherein the two parallel sheets remain parallel after introduction of the biological material, c. sealing package, d. delivering the package to a freezing facility.

6. The method according to claim 5, wherein the package further comprises a second opening arranged for expulsion of air, and wherein the method further comprises expelling air from the second opening upon introduction of the sample and wherein the step of sealing the package comprises sealing the first and second openings.

7. The method according to claim 6 further comprising applying suction to the second opening in order to influence the flow of the sample throughout the package.

* * * * *